(12) United States Patent
Nappa et al.

(10) Patent No.: US 7,981,312 B2
(45) Date of Patent: Jul. 19, 2011

(54) PROCESSES FOR PRODUCING AND COMPOSITIONS COMPRISING 2,3,3,3-TETRAFLUOROPROPENE AND/OR 1,2,3,3-TETRAFLUOROPROPENE

(75) Inventors: Mario Joseph Nappa, Newark, DE (US); Velliyur Mallikarjuna Nott Rao, Wilmington, DE (US); Allen Capron Sievert, Elkton, MD (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 246 days.

(21) Appl. No.: 12/442,952

(22) PCT Filed: Oct. 31, 2007

(86) PCT No.: PCT/US2007/022993
§ 371 (c)(1),
(2), (4) Date: Mar. 26, 2009

(87) PCT Pub. No.: WO2008/054780
PCT Pub. Date: May 8, 2008

(65) Prior Publication Data
US 2010/0025620 A1    Feb. 4, 2010

Related U.S. Application Data

(60) Provisional application No. 60/855,541, filed on Oct. 31, 2006.

(51) Int. Cl.
  *C09K 5/04* (2006.01)
  *C07C 17/20* (2006.01)
  *C07C 17/357* (2006.01)
  *C07C 17/25* (2006.01)

(52) U.S. Cl. ............ 252/67; 570/176; 570/156; 570/177

(58) Field of Classification Search .................... 252/67; 570/176, 156, 177
See application file for complete search history.

(56) References Cited

U.S. PATENT DOCUMENTS

| 5,629,461 | A | 5/1997 | Yasuhara et al. |
| 7,026,520 | B1 | 4/2006 | Mukhopadhyay et al. |
| 7,285,692 | B2 * | 10/2007 | Rao et al. ....................... 570/176 |
| 7,659,435 | B2 * | 2/2010 | Rao et al. ....................... 570/165 |
| 7,678,949 | B2 * | 3/2010 | Rao et al. ....................... 570/156 |
| 7,728,183 | B2 * | 6/2010 | Nappa et al. ................... 570/177 |
| 7,803,975 | B2 * | 9/2010 | Knapp ............................ 570/177 |
| 7,872,161 | B2 * | 1/2011 | Rao et al. ....................... 570/176 |
| 2004/0119047 | A1 | 6/2004 | Singh et al. |
| 2006/0094911 | A1 | 5/2006 | Rao et al. |
| 2006/0106263 | A1 | 5/2006 | Miller et al. |
| 2007/0197841 | A1 * | 8/2007 | Mukhopadhyay et al. ... 570/155 |
| 2008/0207963 | A1 * | 8/2008 | Rao et al. ....................... 570/156 |
| 2009/0012336 | A1 * | 1/2009 | Nappa et al. ................... 570/177 |
| 2010/0051852 | A1 * | 3/2010 | Rao et al. ........................ 252/67 |
| 2010/0294979 | A1 * | 11/2010 | Sievert ............................ 252/67 |
| 2010/0320412 | A1 * | 12/2010 | Nappa et al. .................... 252/67 |

FOREIGN PATENT DOCUMENTS

| WO | 2006/094303 | 9/2006 |
| WO | 2007/053670 | 5/2007 |
| WO | 2008/030444 | 3/2008 |
| WO | 2008/054779 | 5/2008 |

OTHER PUBLICATIONS

CAS reg. No. 754-12-1, Nov. 16, 1984.*
CAS reg. No. 4259-43-2, Nov. 16, 1984.*
CAS reg. No. 1652-81-9, Nov. 16, 1984.*
CAS reg. No. 7125-86-2, Nov. 16, 1984.*
Hazeldine R N et al: "Addition of Free Radicals to Unsaturated Systems. Part XIII. Direction of Radical Addition to Chloro-1:1-Difluoroethylne" Journal of the Chemical Society, Letchworth, GB, 1957, pp. 2193-2196, XP009081235.

* cited by examiner

*Primary Examiner* — Douglas McGinty

(57) ABSTRACT

A process is disclosed for making $CF_3CF=CH_2$ or mixtures thereof with $CHF=CFCHF_2$. The process involves contacting $CCl_3CF_2CF_3$ and optionally $CCl_2FCF_2CClF_2$ with $H_2$ in the presence of a palladium catalyst supported on a support of alumina, fluorided alumina and/or aluminum fluoride, to produce a product mixture including $CH_2=CFCF_3$ (and when $CCl_2FCF_2CClF_2$ is present, $CHF=CFCHF_2$); recovering $CH_2=CFCF_3$ or a mixture thereof with $CHF=CFCHF_2$ from the product mixture. The present invention also provides another process that involves reacting $CCl_3CF_2CF_3$ and optionally $CCl_2FCF_2CClF_2$ with $H_2$ in the presence of a hydrogenation catalyst to form $CH_3CF_2CF_3$ (and when $CCl_2FCF_2CClF_2$ is present, $CH_2FCF_2CHF_2$); dehydrofluorinating; and recovering $CH_2=CFCF_3$ or a mixture thereof with $CHF=CFCHF_2$.

10 Claims, No Drawings

PROCESSES FOR PRODUCING AND COMPOSITIONS COMPRISING 2,3,3,3-TETRAFLUOROPROPENE AND/OR 1,2,3,3-TETRAFLUOROPROPENE

This application represents a national filing under 35 U.S.C. 371 of International Application No. PCT/US2007/022993 filed Oct. 31, 2007, and claims priority of U.S. Provisional Application No. 60/855,541 filed Oct. 31, 2006.

FIELD OF THE INVENTION

The present invention relates to processes that involve the production of halogenated hydrocarbon products comprising 2,3,3,3-tetrafluoropropene and/or 1,2,3,3-tetrafluoropropene and compositions comprising 2,3,3,3-tetrafluoropropene and/or 1,2,3,3-tetrafluoropropene.

BACKGROUND OF THE INVENTION

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a ($CF_3CH_2F$) being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

2,3,3,3-Tetrafluoropropene ($CH_2=CFCF_3$, HFC-1234yf) and 1,2,3,3-tetrafluoropropene ($CHF=CFCHF_2$, HFC-1234ye), both having zero ozone depletion and low global warming potential, have been identified as a potential components in refrigerant blends (see PCT application published as WO 2006/094303). HFC-1234yf has been prepared by reaction of $CH_2ClC_2F_5$ with zinc in ethanol as reported by Haszeldine and Steele in Journal of the Chemical Society, pages 2193-2197 (1957). HFC-1234ye has been prepared as a by-product in the vapor phase fluorination of 3-chloro-1,1,2,2-tetrafluoropropane over a chromium catalysts as disclosed by Yasuhara, et. al. in U.S. Pat. No. 5,629,461. There is a need for new manufacturing processes for the product ion of HFC-1234yf and HFC-1234ye.

SUMMARY OF THE INVENTION

The present invention provides a process for making HFC-1234yf or mixtures thereof with HFC-1234ye. The process comprises contacting $CCl_3CF_2CF_3$ (CFC-215cb), and optionally $CCl_2FCF_2CClF_2$ (CFC-215ca), with hydrogen ($H_2$) in a reaction zone in the presence of a catalyst comprising a catalytically effective amount of palladium supported on a support selected from the group consisting of alumina, fluorided alumina, aluminum fluoride and mixtures thereof, to produce a product mixture comprising HFC-1234yf and, when CFC-215ca is present, HFC-1234ye, wherein the mole ratio of $H_2$ to the total of CFC-215cb and CFC-215ca fed to the reaction zone is between about 1:1 and about 5:1; recovering HFC-1234yf, or a mixture thereof with HFC-1234ye, from the product mixture; and optionally separating at least a portion of any HFC-1234ye in the product mixture from the HFC-1234yf in the product mixture.

The present invention also provides another process for making HFC-1234yf or mixtures thereof with HFC-1234ye. This process comprises (a) reacting CFC-215cb and optionally CFC-215ca with $H_2$ in the presence of a catalytically effective amount of a hydrogenation catalyst to form $CH_3CF_2CF_3$ (HFC-245cb) and, when CFC-215ca is present, $CH_2FCF_2CHF_2$ (HFC-245ca); (b) dehydrofluorinating HFC-245cb, and optionally any HFC-245ca, from (a) to form a product mixture comprising HFC-1234yf and, if HFC-245ca is present, HFC-1234ye; and (c) recovering HFC-1234yf, or a mixture thereof with HFC-1234ye, from the product mixture formed in (b); and optionally (d) separating at least a portion of any HFC-1234ye in the product mixture formed in (b) from the HFC-1234yf in the product mixture formed in (b).

The present invention also provides a composition comprising (a) $CF_2HCF=CFH$ and (b) HF; wherein the HF is present in an effective amount to form an azeotropic combination with $CF_2HCF=CFH$.

The present invention also provides a composition useful as a refrigerant comprising Z-HFC-1234ye.

The present invention also provides a composition useful as a refrigerant comprising E-HFC-1234ye.

The present invention also provides a composition comprising (1) 1234yf, (2) 1234ye and (3) at least one flame-retarding compound.

The present invention also provides a composition useful as a blowing agent comprising Z-HFC-1234ye.

The present invention also provides a composition useful as a blowing agent comprising E-HFC-1234ye.

The present invention also provides a composition useful as a blowing agent comprising (1) 1234yf, (2) 1234ye, and (3) at least one compound selected from the group consisting of $CHF_2CH_3$ (HFC-152a), $CHF_2CHF_2$ (HFC-134), $CF_3CH_2F$ (HFC-134a), $CF_3CH_3$ (HFC-143a), $CF_3CH_2CHF_2$ (HFC-245fa), $CF_3CH=CHCF_3$ (HFC-1336mzz), $CF_3CF=CHF$ (HFC-1225ye), $CF_3CH=CH_2$ (HFC-1243zf), propane, n-butane, isobutane, and dimethyl ether.

The present invention also provides a composition useful as a cleaning agent comprising Z-HFC-1234ye.

The present invention also provides a composition useful as a cleaning agent comprising E-HFC-1234ye.

The present invention also provides a composition useful as a cleaning agent comprising (1) 1234yf, (2) 1234ye, and (3) at least one compound selected from the group consisting of $CH_2Cl_2$, (methylene chloride); $CH_3CCl_3$ (1,1,1-trichloroethane); $CH_2ClCH_2Cl$ (1,2-dichloroethane); E- or Z—CHCl=CHCl (cis or trans-1,2-dichloroethylene); trichloroethylene; perchloroethylene; n-propyl bromide; methanol; ethanol; isopropanol; n-propanol; methyl-t-butyl ether; tetrahydrofuran; dioxane; ethylene glycol dimethyl ether; acetone; methyl ethyl ketone; butyl ethyl ketone; methylacetate; ethylacetate; hexamethyldisiloxane; pentanes; hexanes; heptanes; octanes; hexenes; heptenes; $CF_3CH_2CF_2CH_3$ (HFC-365mfc); $CF_3CHFCHFCF_2CF_3$ (HFC-43-10mee); cyclo-$CF_2CF_2CF_2CHFCH_2$— (HFC-C447fec); $C_4F_9OCH_3$ (HFE-7100); and $C_4F_9OC_2H_5$ (HFE-7200).

The present invention also provides an aerosol cleaning composition comprising (i) HFC-1234yf as an aerosol propellant; (ii) at least one solvent selected from the group consisting of (a) halogenated compounds selected from the group consisting of saturated chlorocarbons, unsaturated chlorocarbons and saturated bromocarbons, (b) oxygen-containing compounds selected from the group consisting of alcohols, ethers, ketones, esters, and siloxanes; and (c) hydrocarbons of the formula $C_nH_{2n+2}$ and hydrocarbons of the formula $C_mH_{2m}$ where m and n are integers from 4 to 8; and (iii) at least one fluorinated compound selected from the group consisting of saturated hydrofluorocarbons, unsaturated hydrofluorocarbons, saturated hydrofluoroethers, unsaturated hydrofluoroethers, and unsaturated halofluorocarbons.

DETAILED DESCRIPTION

The present invention provides a process for making HFC-1234yf or mixtures thereof with 1234ye by reacting at least one compound selected from the group consisting of CFC-215cb and CFC-215ca with hydrogen in a reaction zone over a suitable catalyst. HFC-1234ye may exist as one of two configurational isomers, E or Z. HFC-1234ye as used herein refers to either E-HFC-1234ye (CAS Reg No. [115781-19-6]) or Z-HFC-1234ye (CAS Reg. No. [730993-62-1]), as well as any combination or mixture of such isomers.

Of note are embodiments wherein the $C_3Cl_3F_5$ component (that is, the total of CFC-215cb and CFC-215ca) reacted with hydrogen is primarily CFC-215cb. Of particular note are embodiments where the $C_3Cl_3F_5$ reacted with hydrogen is essentially free of CFC-215ca.

CFC-215cb and CFC-215ca can be prepared from a variety of starting materials. For example, a mixture of CFC-215cb and CFC-215ca can be prepared by the reaction of trichlorofluoromethane (CFC-11) with tetrafluoroethylene (TFE) in the presence of aluminum chloride as reported by Paleta, et. al. in Collections of Czechoslovia Chemical Communications, Vol. 36, pages 1867 to 1875 (1971). However, the boiling points of CFC-215cb and CFC-215ca are within about one degree Celsius of each other making separation by conventional distillation very difficult. In one embodiment of the present invention, it is possible to prepare CFC-215cb essentially free of CFC-215ca by reacting TFE with CFC-11 in the presence of aluminum chlorofluoride in a mole ratio of at least 1:1. Under these conditions CFC-215ca formed as a co-product with CFC-215cb reacts with additional TFE to form $CClF_2CF_2CCl_2C_2F_5$ (CFC-4191ca) (see Example No. 1). When the mole ratio of TFE to CFC-11 is less than one, a substantial amount of CFC-215ca is present in the reaction product (see Example No. 2). The boiling point of CFC-4191ca is substantially higher than CFC-215cb which permits easy separation of CFC-215cb by conventional distillation.

Catalysts suitable for carrying out the process of making HFC-1234 product in accordance with this invention (that is, HFC-1234yf and optionally HFC-1234ye) from $C_3Cl_3F_5$ starting material comprise palladium and may optionally comprise additional Group VIII metals (e.g., Pt, Ru, Rh or Ni). The palladium is supported on alumina, fluorided alumina, aluminum fluoride or a mixture thereof. The palladium-containing precursor used to prepare the catalyst is preferably a palladium salt (e.g., palladium chloride). Other metals, when used, may be added to the support during the preparation of the catalyst.

The supported metal catalysts may be prepared by conventional methods known in the art such as by impregnation of the carrier with a soluble salt of the catalytic metal (e.g., palladium chloride or rhodium nitrate) as described by Satterfield on page 95 of Heterogenous Catalysis in Industrial Practice, $2^{nd}$ edition (McGraw-Hill, New York, 1991). Palladium supported on alumina is available commercially. Another suitable procedure for preparing a catalyst containing palladium on fluorided alumina is described in U.S. Pat. No. 4,873,381, which is incorporated herein by reference.

By a catalytically effective amount is meant the concentration of catalysts on the support that is sufficient to carry out the catalytic reaction. The concentration of palladium on the support is typically in the range of from about 0.1% to about 10% by weight based on the total weight of the catalyst and is preferably in the range of about 0.1% to about 5% by weight based on the total weight of the catalyst. The concentration of the additional Group VIII metal, when used, is about 3% by weight, or less, based on the total weight of the catalyst; but palladium is ordinarily at least 50% by weight based on the weight of the total metals present on the support, and preferably at least 80% by weight based on the weight of the total metals present on the support.

The relative amount of hydrogen fed during contact of $C_3Cl_3F_5$ in a reaction zone containing the palladium-containing catalyst is from about 1 mole of $H_2$ per mole of $C_3Cl_3F_5$ to about 5 moles of $H_2$ per mole of $C_3Cl_3F_5$, preferably from about 1 mole of $H_2$ per mole of $C_3Cl_3F_5$ to about 4 moles of $H_2$ per mole of $C_3Cl_3F_5$ and more preferably from about 1 mole of $H_2$ per mole of $C_3Cl_3F_5$ to about 2 moles $H_2$ per mole of $C_3Cl_3F_5$.

The reaction zone temperature for the catalytic hydrogenation of $C_3Cl_3F_5$ is typically in the range of from about 100° C. to about 400° C., and preferably is in the range of from about 125° C. to about 350° C. The contact time is typically in the range of from about 1 to about 450 seconds, and preferably is in the range of from about 10 to about 120 seconds. The reactions are typically conducted at near atmospheric pressure.

The effluent from the reaction zone typically includes HCl, unreacted hydrogen, HF, $CF_3CF=CH_2$ (HFC-1234yf), $CF_3CF_2CH_3$ (HFC-245cb), higher boiling products and intermediates typically including one or more of $CF_3CF=CCl_2$ (CFC-1214ya), $CF_3CF=CHCl$ (HCFC-1224yd), $CHCl_2CF_2CF_3$ (HCFC-225ca), $CH_2ClCF_2CF_3$ (HCFC-235cb), $CF_3CHFCHClF$ (HCFC-235ea), $CF_3CHFCH_2Cl$ (HCFC-244eb), and any unconverted CFC-215cb. When CFC-215ca is present as a starting material, the effluent from the reaction zone may also include one or more of CFC-1214yb ($CClF=CFCClF_2$), $CClF=CFCHF_2$ (HCFC-1224yb), $CF_2=CFCHClF$ (HCFC-1224yc), $CHClFCF_2CClF_2$ (HCFC-225cb), $CHClFCHFCClF_2$ (HCFC-234eb), $CHClFCF_2CHF_2$ (HCFC-235ca), $CHClFCHFCHF_2$ (HCFC-244ea), $CH_2FCF_2CHF_2$ (HFC-245ca) and any unconverted CFC-215ca.

Of note are embodiments where HFC-1234yf is a desired product, and is recovered from the product mixture. The HFC-1234yf present in the effluent from the reaction zone may be separated from the other components of the product mixture and unreacted starting materials by conventional means (e.g., distillation). When HF is present in the effluent, this separation can also include isolation of azeotrope or near azeotrope composition of HFC-1234yf and HF and further processing to produce HF-free HFC-1234yf by using procedures similar to that disclosed in U.S. Patent Application No. 2006/0106263, which is incorporated herein by reference.

The present invention also provides a process for making HFC-1234 that comprises (a) reacting $C_3Cl_3F_5$ with $H_2$ in a reaction zone in the presence of a catalytically effective amount of hydrogenation catalyst to form $C_3H_3F_5$ (that is, the total of HFC-245cb and any HFC-245ca); and (b) dehydrofluorinating $C_3H_3F_5$ from (a) to form HFC-1234. In step (a) of this process of the invention, $C_3Cl_3F_5$ is reacted with hydrogen in the presence of a hydrogenation catalyst. Hydrogenation catalysts suitable for use in this invention include catalysts comprising at least one catalytic metal component selected from the group consisting of iron, cobalt, rhodium, nickel, palladium, and platinum. Said catalytic metal component is typically supported on a carbonaceous carrier such as activated carbon or graphite or an aluminum-based support such as alumina, fluorided alumina, aluminum fluoride, or mixtures thereof. Of note are carbon-supported catalysts in which the carbon support has been washed with acid and has an ash content below about 0.1% by weight. Hydrogenation catalysts supported on low ash carbon are described in U.S. Pat. No. 5,136,113, the teachings of which are incorporated herein by reference. Of particular note are palladium catalysts supported on carbon (see e.g., U.S. Pat. No. 5,523,501, the teachings of which are incorporated herein by reference). Also of particular note are palladium catalysts supported on three-dimensional matrix porous carbonaceous materials. Preparation of such three-dimensional matrix porous carbonaceous materials is disclosed in U.S. Pat. No. 4,978,649, incorporated herein by reference. Also of note are platinum catalyst supported on alumina, fluorided alumina, aluminum fluoride or a mixture thereof.

Also of note is use of palladium supported on alumina, fluorided alumina, aluminum fluoride or a mixture thereof in step (a) where HFC-1234yf is produced in both step (a) and step (b).

The relative amount of hydrogen contacted with $C_3Cl_3F_5$ is typically from about one mole of hydrogen per mole of $C_3Cl_3F_5$ to about 15 moles of $H_2$ per mole of the $C_3Cl_3F_5$ starting material. Suitable reaction temperatures are typically from about 100° C. to about 350° C., preferably from about 125° C. to about 300° C. The contact time is typically from about 1 to about 450 seconds, preferably from about 10 to about 120 seconds. The reactions are typically conducted at atmospheric or superatmospheric pressures.

The effluent from the reaction zone in this process of the invention typically includes HCl, unreacted hydrogen, HFC-245cb, and one or more of CFC-215cb, CFC-1214ya, HCFC-235cb, and HCFC-225ca. If CFC-215ca is present as a starting material, the effluent from the reaction zone typically also includes HFC-245ca and one or more of CFC-215ca, HCFC-225cb, $CCl_2FCF_2CHF_2$ (HCFC-225 cc), $CH_2FCF_2CClF_2$ (HCFC-235 cc), HCFC-235ca, and CFC-1214yb. In one embodiment of the invention, the HFC-245cb is isolated by separation processes known in the art such as distillation; and the isolated HFC-245cb is then used for step (b) of the process.

Unreacted $C_3Cl_3F_5$ and intermediate products such as $C_3HCl_2F_5$ and $C_3H_2ClF_5$ isomers may be recycled to step (a) of the process. Reaction by-products such as $C_3Cl_2F_4$ isomers may be recovered and converted to HFC-1234 in the reaction zone of step (a) of the process or separately by contact with hydrogen in the presence of a hydrogenation catalyst.

In another embodiment of the invention, the $C_3Cl_3F_5$ is reacted with hydrogen in the presence of catalyst in a molar ratio of $H_2$ to $C_3Cl_3F_5$ of from about 1:1 to about 10:1; and, after separation of hydrogen chloride and any hydrogen, the remaining effluent from the reaction zone is then sent directly to step (b) of the process.

In step (b) of the process of the invention, the $C_3H_3F_5$ produced in step (a) is contacted with a dehydrofluorination catalyst in a reaction zone for time sufficient to convert at least a portion of the $C_3H_3F_5$ to HFC-1234yf and, if HFC-245ca is fed to the reaction zone, HFC-1234ye. The dehydrofluorination reaction may be conducted in a tubular reactor in the vapor phase at temperatures of from about 200° C. to about 500° C. and preferably from about 300° C. to about 450° C. The contact time is typically from about 1 to about 450 seconds, preferably from about 10 to about 120 seconds.

The reaction pressure can be subatmospheric, atmospheric or superatmospheric. Generally, near atmospheric pressures are preferred. However, the dehydrofluorination of $C_3H_3F_5$ can be beneficially run under reduced pressure (i.e., pressures less than one atmosphere).

The catalytic dehydrofluorination can optionally be carried out in the presence of an inert gas such as nitrogen, helium or argon. The addition of an inert gas can be used to increase the extent of dehydrofluorination. Of note are processes where the mole ratio of inert gas to $C_3H_3F_5$ is from about 5:1 to 1:1. Nitrogen is the preferred inert gas.

Typical dehydrofluorination reaction conditions and dehydrofluorination catalysts are disclosed in U.S. Pat. No. 5,396,000, which is herein incorporated by reference in its entirety. Preferably, the dehydrofluorination catalyst comprises at least one catalyst selected from the group consisting of carbon, aluminum fluoride, fluorided alumina, and trivalent chromium oxide.

Other dehydrofluorination catalysts useful for converting $C_3H_3F_5$ from step (a) to HFC-1234 products are described in U.S. Pat. No. 6,093,859; the teachings of this disclosure are incorporated herein by reference in its entirety. Still other dehydrofluorination catalysts suitable for use in step (b) are described in U.S. Pat. No. 6,369,284; the teachings of this disclosure are incorporated herein by reference in its entirety.

The products from the step (b) reaction zone typically include HF, HFC-1234yf, and when HFC-245ca is present, the E- and Z-forms of HFC-1234ye. Unconverted $C_3H_3F_5$ may be recovered and recycled back to the dehydrofluorination reactor to produce additional quantities of HFC-1234.

The separation steps involving recovery of HFC-1234yf and/or HFC-1234ye, such as steps (c) and (d) above, can be carried out using conventional separation technology such as distillation.

The HFC-1234 products produced by the processes of this invention can be recovered individually and/or as mixtures thereof. Of note are processes wherein in step (a) the $C_3Cl_3F_5$ contacted with $H_2$ includes CFC-215ca; wherein the $C_3H_3F_5$ dehydrofluorinated in (b) includes HFC-245ca; and wherein the product mixture formed in (b) includes HFC-1234ye. Included are processes wherein HFC-1234yf essentially free of HFC-1234ye is recovered and/or HFC-1234ye essentially free of HFC-1234yf is recovered.

The consideration of a process for the separation of HFC-1234ye from the product mixture by distillation includes the azeotropic combination thereof with HF.

HFC-1234ye/HF Azeotrope

As noted above, the present invention also provides azeotrope compositions comprising an effective amount of hydrogen fluoride combined with HFC-1234ye.

By effective amount is meant an amount, which, when combined with HFC-1234ye, results in the formation of azeotrope mixture. As recognized in the art, an azeotrope composition is a constant boiling liquid admixture of two or more different substances, wherein the admixture distills without substantial composition change and behaves as a constant boiling composition. Constant boiling compositions, which are a characterized as azeotropic, exhibit either a maximum or a minimum boiling point, as compared with that of the non-azeotropic mixtures of the same substances. Azeotropic compositions as used herein include homogeneous azeotropes, which are liquid admixtures of two or more substances that behave as a single substance, in that the vapor, produced by partial evaporation or distillation of the liquid, has the same composition as the liquid. Azeotropic compositions as used herein also includes heterogeneous azeotropes where the liquid phase splits into two or more liquid phases. In these embodiments, at the azeotropic point, the vapor phase is in equilibrium with two liquid phases and all three phases have different compositions. If the two equilibrium liquid phases of a heterogeneous azeotrope are combined and the composition of the overall liquid phase calculated, this would be identical to the composition of the vapor phase.

Accordingly, the essential features of an azeotrope composition are that at a given pressure, the boiling point of the liquid composition is fixed and that the composition of the vapor above the boiling composition is essentially that of the boiling liquid composition (i.e., no fractionation of the components of the liquid composition takes place). It is also recognized in the art that both the boiling point and the weight percentages of each component of the azeotrope composition may change when the azeotrope composition is subjected to boiling at different pressures. Thus, an azeotrope composition may be defined in terms of the unique relationship that exists among the components or in terms of the compositional ranges of the components or in terms of exact weight percentages of each component of the composition characterized by a fixed boiling point at a specified pressure. It is also recognized in the art that various azeotrope compositions (including their boiling points at particular pressures) may be calculated (see, e.g., W. Schotte Ind. Eng. Chem. Process Des. Dev. (1980) 19, 432-439). Experimental identification of azeotrope compositions involving the same components may be used to confirm the accuracy of such calculations and/or to modify the calculations at the same or other temperatures and pressures.

In accordance with this invention, compositions are provided which comprise the HFC-1234ye and HF, wherein the HF is present in an effective amount to form an azeotropic combination with the HFC-1234ye. According to calculations, these include compositions comprising from about 80 mole percent to about 60 mole percent HF and from about 20 mole percent to about 40 mole percent HFC-1234ye (which form azeotropes boiling at a temperature of from between about 0° C. and about 100° C.).

Compositions may be formed that consist essentially of azeotrope combinations of hydrogen fluoride with HFC-1234ye. These include compositions calculated to consist essentially of from about 80 mole percent to about 60 mole percent HF and from about 20 mole percent to about 40 mole percent HFC-1234ye (which forms an azeotrope boiling at a temperature from between about 0° C. and about 100° C.).

Azeotropic compositions of HF and HFC-1234ye are useful as sources of HF in fluorination reactions. For example by combining the azeotrope of HF and HFC-1234ye with fluorination precursor compounds it is possible to obtain HF-free HFC-1234ye and a fluorinated product (see for example, U.S. Pat. No. 6,224,781).

The reactor, distillation columns, and their associated feed lines, effluent lines, and associated units used in applying the process of this invention should be constructed of materials resistant to hydrogen fluoride and hydrogen chloride. Typical materials of construction, well-known to the fluorination art, include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

The HFC-1234yf, the Z isomer of HFC-1234ye, and the E isomer of HFC-1234ye are all useful (both individually and as mixtures thereof) as components of refrigerant compositions, blowing agent compositions, sterilant compositions, aerosol propellant compositions, and cleaning compositions. Of note are compositions comprising HFC-1234yf, HFC-1234ye, and at least one flame retarding compound. Included are compositions wherein the flame retarding component comprises at least one compound selected from the group consisting of hydrofluorocarbons, hydrochlorofluorocarbons, perfluorocarbons, perfluoroketones, bromoperfluoroketones, perfluorosulfones, hydrofluorosulfones, bromofluorosulfones, perfluoropolyethers, hydrofluoropolyethers, hydrofluoroethers, chlorofluorocarbons, bromofluorocarbons, bromochlorofluorocarbons, hydrobromocarbons, iodofluorocarbons, and hydrobromofluorocarbons. This group includes both saturated and unsaturated compounds. For example, the term "bromofluorocarbon" includes bromofluoroalkanes as well as bromofluoroolefins and the term "hydrofluorocarbon" includes hydrofluoroalkanes as well as hydrofluoroolefins. Of note are compositions wherein the flame-retarding component comprises HFC-1225ye ($CF_3CF=CHF$), HFC-125 ($CF_3CHF_2$), HFC-23 ($CHF_3$), HFC-227ea ($CF_3CHFCF_3$), HFC-236fa ($CF_3CH_2CF_3$), $CF_3I$ and/or $CF_3CBr=CH_2$.

Also of note are compositions wherein the flame-retarding component comprises carbon dioxide and the carbon dioxide is at least about 20 weight percent of the composition. Of note are such compositions wherein the HFC-1234ye therein consists essentially of the Z isomer. Also of note are such compositions wherein the HFC-1234ye therein consists essentially of the E isomer.

This invention provides certain refrigerant compositions comprising HFC-1234ye. In one embodiment, the refrigerant compositions comprise Z-HFC-1234ye. In another embodiment, the refrigerant compositions comprise E-HFC-1234ye. These compositions may further comprise other components as described for example in PCT application published as WO2006/094303, which is hereby incorporated by reference in its entirety. Of particular note are refrigerant compositions comprising Z-HFC-1234ye and $CF_3I$. These compositions may also comprise E-HFC-1234ye. Of note are refrigerant compositions wherein the HFC-1234ye therein consists essentially of the Z isomer. Also of note are refrigerant compositions wherein the HFC-1234ye therein consists essentially of the E isomer.

This invention also provides certain blowing agent compositions comprising HFC-1234ye and HFC-1234yf. Certain of these compositions may be used for example in methods to produce foams of thermoset and thermoplastic resins. These compositions may further comprise other components as described for example in U.S. Pat. Nos. 5,147,896 and 5,164,419, both of which are hereby incorporated by reference in their entirety. In one embodiment, a blowing agent composition is provided that comprises Z-HFC-1234ye. In another embodiment, a blowing agent composition is provided that comprises E-HFC-1234ye. In yet another embodiment, a blowing agent composition is provided that comprises HFC-1234ye, HFC-1234yf and at least one compound selected from the group consisting of HFC-152a ($CH_2FCH_2F$), HFC-134 ($CHF_2CHF_2$), HFC-134a ($CF_3CH_2F$), HFC-143a ($CF_3CH_3$), HFC-245fa ($CF_3CH_2CHF_2$), HFC-1336mzz ($CF_3CH=CHCF_3$), HFC-1225ye ($CF_3CF=CHF$), HFC-1243zf $CF_3CH=CH_2$), propane, n-butane, and dimethyl ether. Of note are blowing agent compositions wherein the HFC-1234ye therein consists essentially of the Z isomer. Also of note are blowing agent compositions wherein the HFC-1234ye therein consists essentially of the E isomer.

This invention provides cleaning compositions. In one embodiment, a cleaning composition is provided that comprises Z-HFC-1234ye. In another embodiment, a cleaning composition is provided that comprises E-HFC-1234ye.

In yet another embodiment, a cleaning composition is provided that comprises HFC-1234ye, HFC-1234yf and at least one compound selected from the group consisting of $CH_2Cl_2$, (methylene chloride); $CH_3CCl_3$ (1,1,1-trichloroethane);

CH$_2$ClCH$_2$Cl (1,2-dichloroethane); E- or Z—CHCl=CHCl (cis or trans-1,2-dichloroethylene); trichloroethylene; perchloroethylene; n-propyl bromide; methanol; ethanol; isopropanol; n-propanol; methyl-t-butyl ether; tetrahydrofuran; dioxane; ethylene glycol dimethyl ether; acetone; methyl ethyl ketone; butyl ethyl ketone; methylacetate; ethylacetate; hexamethyldisiloxane; pentanes; hexanes; heptanes; octanes; hexenes; heptenes; CF$_3$CH$_2$CF$_2$CH$_3$ (HFC-365mfc); CF$_3$CHFCHFCF$_2$CF$_3$ (HFC-43-10mee); cyclo-CF$_2$CF$_2$CF$_2$CHFCH$_2$— (HFC-C447fec); C$_4$F$_9$OCH$_3$ (HFE-7100); C$_4$F$_9$OC$_2$H$_5$ (HFE-7200). These cleaning compositions may further comprise other components as described for example in U.S. Pat. No. 6,852,684, which is hereby incorporated by reference in its entirety. Of note are cleaning compositions wherein the HFC-1234ye therein consists essentially of the Z isomer. Also of note are such compositions wherein the HFC-1234ye therein consists essentially of the E isomer.

This invention also provides aerosol compositions comprising HFC-1234yf. Of particular note are aerosol cleaning compositions comprising: (i) HFC-1234yf as an aerosol propellant; (ii) at least one solvent selected from the group consisting of (a) halogenated compounds selected from the group consisting of saturated chlorocarbons, unsaturated chlorocarbons and saturated bromocarbons, (b) oxygen-containing compounds selected from the group consisting of alcohols, ethers, ketones, esters, and siloxanes and (c) hydrocarbons of the formula C$_n$H$_{2n+2}$ and hydrocarbons of the formula C$_m$H$_{2m}$ where m and n are integers from 4 to 8; and (iii) at least one fluorinated compound selected from the group consisting of saturated hydrofluorocarbons, unsaturated hydrofluorocarbons, saturated hydrofluoroethers, unsaturated hydrofluoroethers, and unsaturated halofluorocarbons.

Examples of component (ii) include CH$_2$Cl$_2$, (methylene chloride); CH$_3$CCl$_3$ (1,1,1-trichloroethane); CH$_2$ClCH$_2$Cl (1,2-dichloroethane); E- and/or Z—CHCl=CHCl (cis and/or trans-1,2-dichloroethylene); trichloroethylene; perchloroethylene; n-propyl bromide; methanol; ethanol; isopropanol; n-propanol; methyl-t-butyl ether; tetrahydrofuran; dioxane; ethylene glycol dimethyl ether; acetone; methyl ethyl ketone; butyl ethyl ketone; methylacetate; ethylacetate; hexamethyldisiloxane; pentanes; hexanes; heptanes; octanes; hexenes; and heptenes.

Examples of component (iii) include HFC-1234ye, HFC-43-10mee, HFC-365mfc, HFC-245fa, HFC-C447fec, CF$_3$CF$_2$CH=CHCF$_2$CF$_2$CF$_3$ (F24E), HFE-7100, and HFE-7200 and others as described in for example U.S. Pat. No. 6,852,684, and U.S. Provisional Patent Application No. 60/732,771. Of note are aerosol cleaning compositions that comprise at least one compound selected from the group consisting of HFC-1234ye, HFC-43-10mee, HFC-365mfc, HFC-C447fec, CF$_3$CF$_2$CH=CHCF$_2$CF$_2$CF$_3$ (F24E), HFE-7100, and HFE-7200.

The following specific Examples are to be construed as merely illustrative, and do not constrain the remainder of the disclosure in any way whatsoever.

EXAMPLES

LEGEND

| | |
|---|---|
| 215aa is CF$_3$CCl$_2$CClF$_2$ | 215cb is CF$_3$CF$_2$CCl$_3$ |
| 216cb is CCl$_2$FCF$_2$CF$_3$ | 225ca is CHCl$_2$CF$_2$CF$_3$ |
| 235cb is CH$_2$ClCF$_2$CF$_3$ | 235cc is CH$_2$FCF$_2$CClF$_2$ |
| 244 is C$_3$H$_3$ClF$_4$ | 245cb is CF$_3$CF$_2$CH$_3$ |
| 254eb is CF$_3$CHFCH$_3$ | 263fb is CF$_3$CH$_2$CH$_3$ |
| 1234yf is CF$_3$CF=CH$_2$ | |

Example 1

Reaction of CFC-11 with TFE

A 400 mL Hastelloy™ C shaker tube was charged with aluminum chlorofluoride (7 g) and CFC-11 (69 g, 0.50 mole). The aluminum chlorofluoride was prepared according to the procedure in U.S. Pat. No. 5,157,171. The tube was cooled in dry ice, evacuated, and purged three times with nitrogen. The cold tube was placed in the barricade, charged with 20 g of TFE (0.20 mole), and heated to 41° C. Another 30 g of TFE (0.50 mole total) was added; the maximum pressure was 58 psig. The tube was held at 37-41° C. for 4 h; the final pressure was 8 inches of vacuum. The product was discharged to give 124 g of a clear supernatant over a brown solid. Analysis of the product by $^{19}$F NMR is given in the Table below.

| Component | Formula | GC % |
|---|---|---|
| CFC-216ca + cb | C$_3$Cl$_2$F$_6$ | 3.5 |
| CFC-215aa | CClF$_2$CCl$_2$CF$_3$ | 1.1 |
| CFC-215cb | CCl$_3$CF$_2$CF$_3$ | 68.9 |
| CFC-215ca | CCl$_2$FCF$_2$CClF$_2$ | a |
| CFC-214cb | CCl$_3$CF$_2$CClF$_2$ | 3.5 |
| CFC-419lca | CClF$_2$CF$_2$CCl$_2$CF$_2$CF$_3$ | 13.5 |
| CFC-41-10mca | CF$_3$CF$_2$CCl$_2$CF$_2$CF$_3$ | 3.3 | a. Overlap with CFC-215cb in GC trace. 19F NMR shows 0.8 mole % CFC-215ca.

Example 2

Reaction of CFC-11 with TFE

A suspension of aluminum chlorofluoride (15 g) in CFC-11 (600 g, 4.37 moles) was drawn into an evacuated, 1 L stirred autoclave. The reactor already contained spent catalyst from the previous similar run. d-Limonene-inhibited TFE was fed to the reactor beginning at a temperature of 15.4° C. and a pressure of 6.3 psig. A total of 410.6 g of TFE (4.11 moles) were added to the autoclave over the course of about 0.72 h. The reaction exotherm brought the temperature in the reactor to 40.2° C. The reaction was then cooled and the products discharged to afford 906.9 g of crude product which was analyzed by $^{19}$F NMR with the results given below.

| Component | Formula | GC % |
|---|---|---|
| CFC-12 | CCl$_2$F$_2$ | 0.5 |
| CFC-11 | CCl$_3$F | 0.5 |
| HCC-10 | CCl$_4$ | 3.0 |
| CFC-216cb + ca | C$_3$Cl$_2$F$_6$ | 2.3 |
| CFC-215cb | CCl$_3$CF$_2$CF$_3$ | 71.8 |
| CFC-215ca | CCl$_2$FCF$_2$CClF$_2$ | 10.8 |
| CFC-214cb | CCl$_3$CF$_2$CClF$_2$ | 3.8 |
| CFC-41-10mca | CF$_3$CF$_2$CCl$_2$CF$_2$CF$_3$ | 1.4 |
| CFC-419lca | CClF$_2$CF$_2$CCl$_2$CF$_2$CF$_3$ | 3.0 |

Example 3

Synthesis of $CF_3CF=CH_2$ by Dehydrofluorination with Fluorided Alumina Catalyst A Hastelloy™ tube reactor (2.54 cm OD×2.17 cm ID×24.1 cm L) was filled with 25 cc of gamma-alumina ground to 12-20 mesh (0.84 to 1.68 mm). The catalyst was activated by heating at 200° C. for 15 minutes under a nitrogen purge and then reacted with a HF/N$_2$ mixture heated up to 425° C. to yield 16.7 gm of activated fluorided alumina.

At a temperature of 350° C., 10 sccm of nitrogen ($1.7 \times 10^{-7}$ m$^3$/s) and 15 sccm ($2.5 \times 10^{-7}$ m$^3$/s) of $CF_3CF_2CH_3$ were mixed and flowed through the reactor. The temperature was then raised to 400° C., the flow rates held constant. The effluent for both temperatures was sampled and analyzed by $^{19}$F NMR. Additionally, the effluent was analyzed by GC to determine concentrations as listed in Table 1.

TABLE 1

| Temp., °C. | N$_2$ flow (sccm) | $CF_3CF_2CH_3$ flow (sccm) | Concentrations, (Mole %) | | |
|---|---|---|---|---|---|
| | | | $CF_3CF=CH_2$ | $CF_3CF_2CH_3$ | Unks |
| 350 | 10 | 15 | 84.2 | 12.8 | 3.0 |
| 400 | 10 | 15 | 91.3 | 1.9 | 6.8 |

Unks = unknowns

Example 4

Synthesis of $CF_3CF=CH_2$ with Carbon Catalyst

Following the procedure of Example 3, a mixture of 10 sccm ($1.7 \times 10^{-7}$ m$^3$/s) of nitrogen and 15 sccm ($2.5 \times 10^{-7}$ m$^3$/s) of $CF_3CF_2CH_3$ were passed through the reactor giving a contact time of 60 seconds. The flows were reduced to 5 sccm ($8.3 \times 10^{-8}$ m$^3$/s) of nitrogen and 7.5 sccm ($1.3 \times 10^{-7}$ m$^3$/s) of $CF_3CF_2CH_3$ giving a contact time of 120 seconds. The effluent was sampled under both sets of conditions and analyzed by $^{19}$F NMR. The effluent compositions as determined by GC are listed in Table 2.

TABLE 2

| Temp., °C. | N$_2$ flow (sccm) | $CF_3CF_2CH_3$ flow (sccm) | Concentrations, Mole % | | |
|---|---|---|---|---|---|
| | | | $CF_3CF=CH_2$ | $CF_3CF_2CH_3$ | Unks |
| 400 | 10 | 15 | 6.0 | 93.9 | 0.1 |
| 400 | 5 | 7.5 | 22.8 | 76.4 | 0.8 |

Unks = unknowns

Example 5

Synthesis of $CHF_2CF=CHF$ from $CHF_2CF_2CH_2F$

A 0.375 inch (0.95 cm) O.D. Hastelloy™ nickel alloy tube was charged with 7.0 grams (10 cc) of gamma-alumina ground to 12/20 mesh (0.84 to 1.68 mm). The tube was purged with nitrogen (50 sccm, $8.3 \times 10^{-7}$ m$^3$/s) for twenty minutes as the temperature was raised from 40° C. to 175° C. The nitrogen flow was continued as anhydrous hydrogen fluoride (50 sccm, $8.3 \times 10^{-7}$ m$^3$/s) was added to the reactor for about 1.5 hours. The nitrogen flow was then reduced to 20 sccm ($3.3 \times 10^{-7}$ m$^3$/s) and the hydrogen fluoride flow increased to 80 sccm ($1.3 \times 10^{-6}$ m$^3$/s) as the temperature in the tube was increased from 174° C. to 373° C. over the course of 3.7 hours. The nitrogen flow was then reduced to 10 sccm ($1.7 \times 10^{-7}$ m$^3$/s) and the hydrogen fluoride flow was maintained at 80 sccm ($1.3 \times 10^{-6}$ m$^3$/s) for one hour at 400° C. The reactor temperature was then adjusted to 290° C. and the reactor purged with nitrogen.

$CHF_2CF_2CH_2F$ was vaporized and fed to the reactor at such a rate as to maintain a contact time with the catalyst of 120 seconds. No nitrogen co-feed was present. Gas chromatographic analyses of the reactor effluent at three temperatures are listed in Table 3.

TABLE 3

| | GC Area Percent | | |
|---|---|---|---|
| Reactor Temp., °C. | $CHF_2CF_2CH_2F$ | $CHF_2CHFCHF_2$ | E and Z-$CHF_2CF=CHF$ |
| 275 | 72.3 | 5.5 | 22.0 |
| 325 | 40.8 | 6.9 | 51.7 |
| 375 | 27.0 | 3.2 | 68.9 |

Example 6

Hydrodechlorination of CFC-215cb over Fluorided Pd/Al$_2$O$_3$ Catalyst

A commercial palladium on aluminum oxide catalyst (0.5% Pd/Al$_2$O$_3$, 10 cc, 14.45 g, 12-20 mesh (1.68-0.84 mm)) was placed in a 30.5 cm×1.27 cm o.d. Hastelloy® tube. The tube was connected to a reactor system and surrounded with an electrically-heated furnace. The catalyst was first dried for three hours under a nitrogen purge (25 sccm, $4.2 \times 10^{-7}$ m$^3$/s) as the temperature of the furnace was raised to 300° C. The reactor was allowed to cool to 150° C., and then hydrogen gas (20 sccm, $3.3 \times 10^{-7}$ m$^3$/s) was passed through the reactor for three hours as the temperature in the reactor was increased to 300° C. The reactor was cooled again to 150° C. under a flow of nitrogen (20 sccm, $3.3 \times 10^{-7}$ m$^3$/s). The catalyst was then fluorinated with mixture of nitrogen and hydrogen fluoride according to following sequence: 2 hours with N$_2$ flow of $7.5 \times 10^{-7}$ m$^3$/s, and HF flow of $8.3 \times 10^{-8}$ m$^3$/s at 150° C.; 2 hours with N$_2$ flow of $6.6 \times 10^{-7}$ m$^3$/s, and HF flow of $1.7 \times 10^{-7}$ m$^3$/s at 150° C.; 2 hours with N$_2$ flow of $6.6 \times 10^{-7}$ m$^3$/s, and with HF flow of $1.7 \times 10^{-7}$ m$^3$/s at 200° C.; 2 hours with N$_2$ flow of $6.6 \times 10^{-7}$ m$^3$/s, and HF flow of $1.7 \times 10^{-7}$ m$^3$/s at 250° C.; and 2 hours with N$_2$ flow of $4.2 \times 10^{-7}$ m$^3$/s and HF flow of $4.2 \times 10^{-7}$ m$^3$/s at 250° C. The flow of hydrogen fluoride was then stopped and the reactor was purged with nitrogen.

A mixture of hydrogen, $CF_3CF_2CCl_3$ (CFC-215cb), and hydrogen fluoride in a 1:1:2 molar ratio was fed to the above catalyst at 350° C. with a contact time of 25 seconds. The analysis of the reactor effluent as determined by GC-MS is given in TABLE 4.

TABLE 4

| Ex. No. | HFC-245cb | HFC-1234yf | HCFC-235cc | HCFC-235cb | CFC-216cb | HCFC-225ca | CFC-215aa | CFC-216cb | $C_6$ cpds |
|---|---|---|---|---|---|---|---|---|---|
| 6[a] | 19.5 | 6.2 | 0.6 | 0.1 | 4.9 | 10.4 | 2.1 | 44.7 | 9.9 |

[a]$C_6$ cpds are a mixture of reductive coupling products E/Z-$C_2F_5$CCl=CCl$C_2F_5$ and $C_2F_5$C=CCl$C_2F_5$.

Example 7

Hydrodechlorination of CFC-215cb over Fluorided Pd/Al$_2$O$_3$ Catalyst

A mixture of hydrogen, $CF_3CF_2CCl_3$ (CFC-215cb), and hydrogen fluoride in a 2:1:2 molar ratio was fed to the above catalyst at 350° C. with a contact time of 20 seconds. The analysis of the reactor effluent as determined by GC-MS is given in TABLE 5.

TABLE 5

| Ex. No. | HFC-245cb | HFC-1234yf | HCFC-235cc | HCFC-235cb | CFC-216cb | HCFC-225ca | CFC-215aa | CFC-216cb | $C_6$ cpds |
|---|---|---|---|---|---|---|---|---|---|
| 7[a,b] | 57.8 | 7.3 | 1.7 | 0.8 | 3.2 | 7.3 | 0.5 | 3.6 | 11.1 |

[a]$C_6$ cpds are a mixture of reductive coupling products E/Z-$C_2F_5$CCl=CCl$C_2F_5$ and $C_2F_5$C=CCl$C_2F_5$.
[b]0.5% 254eb also observed.

Example 8

Hydrodechlorination of CFC-215Cb Over Fluorided Pt/Al$_2$O$_3$ Catalyst

A commercial platinum on aluminum oxide catalyst (5% Pt/Al$_2$O$_3$, 10 cc, 9.42 g, 12-20 mesh (1.68-0.84 mm)) was placed in a 30.5 cm×1.27 cm o.d. Hastelloy® tube. The tube was connected to a reactor system and surrounded with a electrically-heated furnace. The catalyst was first dried, reduced, and fluorinated as described in Example 6.

A mixture of hydrogen and $CF_3CF_2CCl_3$ (CFC-215cb) in a 4:1 molar ratio was fed to the above catalyst at 250° C. with a contact time of 30 seconds. The analysis of the reactor effluent as determined by GC-MS is given in TABLE 5.

TABLE 5

| Ex. No. | HFC-245cb | HFC-263fb | HFC-254eb | HCFC-244 | HCFC-235cc | HCFC-235cb | CFC-216cb | HCFC-225ca | CFC-215aa |
|---|---|---|---|---|---|---|---|---|---|
| 8 | 79.3 | 1.2 | 0.8 | 1.3 | 0.6 | 9.3 | 4.8 | 1.1 | 2.9 |

What is claimed is:

1. A process for making $CH_2$=CF$CF_3$ or mixtures thereof with CHF=CFCHF$_2$, comprising:

contacting $CCl_3CF_2CF_3$ and optionally $CCl_2FCF_2CClF_2$ with $H_2$ in a reaction zone in the presence of a catalyst comprising a catalytically effective amount of palladium supported on a support selected from the group consisting of alumina, fluorided alumina, aluminum fluoride and mixtures thereof, to produce a product mixture comprising $CH_2$=CF$CF_3$ and, when $CCl_2FCF_2CClF_2$ is present, CHF=CFCHF$_2$, wherein the mole ratio of $H_2$ to the total of $CCl_3CF_2CF_3$ and $CCl_2FCF_2CClF_2$ fed to the reaction zone is between about 1:1 and about 5:1;

recovering $CH_2$=CF$CF_3$ or a mixture thereof with CHF=CFCHF$_2$ from the product mixture; and optionally separating at least a portion of any CHF=CFCHF$_2$ in the product mixture from the $CH_2$=CF$CF_3$ in the product mixture.

2. The process of claim 1 wherein the $C_3Cl_3F_5$ contacted with $H_2$ is primarily $CCl_3CF_2CF_3$.

3. The process of claim 1 wherein the $C_3Cl_3F_5$ contacted with $H_2$ is produced by reacting $CF_2$=CF$_2$ with $CCl_3F$.

4. The process of claim 3 wherein the molar ratio of $CF_2$=CF$_2$ to $CCl_3F$ is greater than 1:1 and wherein a mixture of $CCl_3CF_2CF_3$ and $CClF_2CF_2CCl_2CF_2CF_3$ is produced.

5. The process of claim 1 wherein the $C_3Cl_3F_5$ contacted with $H_2$ includes $CCl_2FCF_2CClF_2$ and the product mixture includes CHF=CFCHF$_2$.

6. A process for making $CH_2$=CF$CF_3$ or mixtures thereof with CHF=CFCHF$_2$ comprising:

(a) reacting $CCl_3CF_2CF_3$ and optionally $CCl_2FCF_2CClF_2$ with $H_2$ in the presence of a catalytically effective amount of a hydrogenation catalyst to form $CH_3CF_2CF_3$ and if $CCl_2FCF_2CClF_2$ is present, $CH_2FCF_2CHF_2$;

(b) dehydrofluorinating $CH_3CF_2CF_3$ and optionally any $CH_2FCF_2CHF_2$ from (a) to form a product mixture comprising $CH_2$=CF$CF_3$, and when $CH_2FCF_2CHF_2$ is present, CHF=CFCHF$_2$;

(c) recovering $CH_2$=CF$CF_3$ or a mixture thereof with CHF=CFCHF$_2$ from the product mixture formed in (b); and optionally (d) separating at least a portion of any CHF=CFCHF$_2$ in the product mixture formed in (b) from the $CH_2$=CF$CF_3$ in the product mixture formed in (b).

7. The process of claim 6 wherein the said $C_3Cl_3F_5$ contacted with $H_2$ includes $CCl_2FCF_2CClF_2$; wherein the $CH_2FCF_2CHF_2$ produced in (a) is separated from $CH_3CF_2CF_3$ produced in (a); and wherein the $C_3H_3F_5$ dehydrofluorinated in (b) is essentially free of $CH_2FCF_2CHF_2$.

8. The process of claim 6 wherein the said $C_3Cl_3F_5$ contacted with $H_2$ includes $CCl_2FCF_2CClF_2$; wherein the $C_3H_3F_5$ dehydrofluorinated in (b) includes $CH_3CF_2CF_3$; and wherein the product mixture formed in (b) includes $CHF=CFCHF_2$.

9. The process of claim 8 wherein the $CH_2=CFCF_3$ essentially free of $CHF=CFCHF_2$ is recovered.

10. The process of claim 8 wherein the $CHF=CFCHF_2$ essentially free of $CH_2=CFCF_3$ is recovered.

* * * * *